United States Patent [19]
Ohi

[11] 4,054,580
[45] Oct. 18, 1977

[54] PROCESS FOR PRODUCING 2,2,4-TRIMETHYL-6-HYDROXY-7-SUBSTITUTED CHROMANS

[75] Inventor: Reiichi Ohi, Tokyo, Japan

[73] Assignee: Fuji Photo Film Co., Ltd., Minami-ashigara, Japan

[21] Appl. No.: 639,510

[22] Filed: Dec. 10, 1975

[30] Foreign Application Priority Data

Dec. 10, 1974 Japan .................................. 49-142159

[51] Int. Cl.² .......................................... C07D 311/72
[52] U.S. Cl. ................................................ 260/345.5
[58] Field of Search ........................... 260/345.5, 345.3

[56] References Cited

U.S. PATENT DOCUMENTS 3,651,113   3/1972   Metlesics et al. ................. 260/345.5

*Primary Examiner*—James O. Thomas, Jr.
*Assistant Examiner*—Nicky Chan
*Attorney, Agent, or Firm*—Sughrue, Rothwell, Mion, Zinn and Macpeak

[57] ABSTRACT

A process for producing 2,2,4-trimethyl-6-hydroxy-7-substituted chromans which comprises reacting 2-substituted hydroquinones with 2-methyl-2,4-pentanediol in the presence of a Friedel-Crafts catalyst.

8 Claims, No Drawings

PROCESS FOR PRODUCING 2,2,4-TRIMETHYL-6-HYDROXY-7-SUBSTITUTED CHROMANS

BACKGROUND OF THE INVENTION

1. Field of the Invention

This invention relates to a process for producing 6-hydroxychroman derivatives, more particularly, to a process for producing 2,2,4-trimethyl-6-hydroxy-7-substituted chromans.

2. Description of the Prior Art

It is known that 6-hydroxychroman derivatives are effective as antioxidants for gasoline, oils and fats, and other organic compounds, as described in U.S. Pat. No. 2,535,058. Also, British patent specification No. 1,141,812 discloses that they are effective as agents for preventing the deterioration of a color photographic light-sensitive image due to light irradiation. Further, they are used as agents for preventing the thermal deterioration of polyester resins, as described in Japanese Patent Application (OPI) 30,754/72. The products of the present invention can be used for any of the uses set forth above.

At present, the 6-hydroxychroman derivatives which are useful in many areas are not produced industrially in any volume, because few methods are industrially advantageous for producing the same. For example, U.S. Pat. No. 2,535,058 discloses a method of synthesizing 2,2-dimethyl-6-hydroxychroman by reacting 4-methoxyphenol and isoprene with anhydrous hydrogen chloride in glacial acetic acid at 0° C to form 2-γ-dimethacryl-4-methoxyphenol and then heating the same with hydrogen bromide in glacial acetic acid. However, this method is complicated in operation and equipment since two reaction steps are required.

On the other hand, British patent specification No. 1,141,812 describes a method of synthesizing 6-hydroxychroman derivatives by reacting alkyl-substituted hydroquinones with a conjugated diene compound in the presence of zinc chloride. This method is, however, not advantageous on an industrial scale since the conjugated diene compounds used as a reaction reagent are generally costly.

SUMMARY OF THE INVENTION

This invention provides a simple process for producing 6-hydroxychroman derivatives which uses starting materials of low cost, i.e., this invention provides a process for producing 2,2,4-trimethyl-6-hydroxy-7-substituted chromans which comprises reacting 2-substituted hydroquinones with 2-methyl-2,4-pentane-diol in the presence of a Friedel-Crafts catalyst.

DETAILED DESCRIPTION OF THE INVENTION

The 2-substituted hydroquinones used in this invention include hydroquinones which are substituted at the 2-position thereof with an alkyl group, alkenyl group or an aryl group, which term includes monocyclic or dicyclic aryl groups. Of these substituents, those which are so bulky as to exert steric hindrance to prevent reaction of a hydroxy group adjacent the 2-position are preferred in this invention.

Examples of such substituents are long straight chain alkyl groups having 6 or more carbon atoms, preferably 6 to 18 carbon atoms; branched alkyl groups such as isopropyl, t-butyl and 1',1',3',3'-tetramethylbutyl, preferably having 3 to 18 carbon atoms; straight chain alkenyl groups having 6 or more carbon atoms, preferably 6 to 18 carbon atoms; branched alkenyl groups such as isopropenyl, preferably those having 3 to 18 carbon atoms; and aryl groups such as phenyl, naphthyl, and phenyl or naphthyl substituted with one or more of an alkyl group having 1 to 12 carbon atoms such as a methyl, ethyl, butyl, octyl, etc., group, a nitro group, an amino group, an acyl group having 2 to 13 carbon atoms such as acetyl, butyryl, benzoyl, etc., group, a carboxyl group, a sulfo group, or the like.

Specific examples of the 2,2,4-trimethyl-6-hydroxy-7-substituted chroman derivatives obtained according to the process of this invention are given below.

(1) 2,2,4,7-tetramethyl-6-hydroxychroman
(2) 2,2,4-trimethyl-6-hydroxy-7-butenylchroman
(3) 2,2,4-trimethyl-6-hydroxy-7-n-hexanechroman
(4) 2,2,4-trimethyl-6-hydroxy-7-isopropylchroman
(5) 2,2,4-trimethyl-6-hydroxy-7-t-butylchroman
(6) 2,2,4-trimethyl-6-hydroxy-7-(1',1',3',3'-tetramethylbutyl)-chroman
(7) 2,2,4-trimethyl-6-hydroxy-7-phenylchroman
(8) 2,2,4-trimethyl-6-hydroxy-7-nitrophenylchroman
(9) 2,2,4-trimethyl-6-hydroxy-7-sulfonaphthylchroman The condensation reaction of this invention may advantageously be effected, if desired, using a solvent capable of dissolving the starting materials as is conventionally used in a Friedel-Crafts reaction. Suitable solvents include alcohols such as methanol, ethanol and isopropanol, ethylene glycol monoalkyl ethers (having as an alkyl moiety, methyl, ethyl, butyl, etc.), amides such as acetamide and dimethylformamide, ethers such as diethyl ether and dioxane, organic acids such as formic acid, oxalic acid, acetic acid, and particularly, glacial acetic acid, etc. The solvents, while optional, may be used alone or as a mixture thereof. There is no special limitation on the ratio of solvent to reactant. As will be appreciated by one skilled in the art, of course, the amount of solvent should be sufficient to dissolve the reactants and should not be so excessive that high heat loads are required for solvent recovery.

In this invention, the reaction is carried out in the presence of a Friedel-Crafts catalyst. Examples of such catalysts are aluminium chloride, ferric chloride, stannic chloride, zinc chloride, sulfuric acid and polyphosphoric acid. Numerous other useful catalysts are disclosed in George A. Olah, *Friedel-Crafts and Related Reactions*, Vols. I – IV, Interscience Publishers (1963), in particular, Vol. I, Chapter 4 which discloses both useful solvents and catalysts.

In effecting the reaction, the diol compound is added in an amount of about 1 to about 3 mols, more preferably 1 to 1.3 mols, per mol of the 2-substituted hydroquinone.

The amount of the Friedel-Crafts catalyst added depends on the type of the catalyst, but, in general, a suitable amount is about 0.5 to about 5.0 mols per mol of the 2-substituted hydroquinone.

The reaction temperature can be freely varied. If a solvent is used it is lower than the boiling point of a solvent used, but the reaction is preferably effected at a temperature around 0° C at its beginning if a solvent is used or not.

The reaction is conveniently conducted at atmospheric pressure, but may be conducted at super-atmospheric pressure, if desired.

The time of reaction is not limited and, typically, the reaction is merely effected at the above conditions until the desired amount of product is obtained.

The diols which are used in this invention are the most inexpensive of the reaction reagents used for the preparation of the 6-hydroxychromans which have so far been reported. For example, considering that 2,5-dimethyl-2,4-hexadiene, one of the two types of dienes described in British patent specification No. 1,141,812 which discloses a preparation process using 2-substituted hydroquinone derivatives as in this invention, is about 13 times higher in cost per kg than 2-methyl-2,4-pentanediol used in this invention (refer to Eastman Kodak Company Catalogue No. 46, Eastman Organic Chemicals (1971)) and it is used in almost the same amount (at least in an amount about equimolar to the hydroquinone derivative used), it can be said that the reaction reagent used in this invention is very inexpensive.

The use of starting materials of low cost facilitates industrialization. Also, it is advantageous that the reaction can be completed in one step. Moreover, according to the process of this invention, 6-hydroxychroman derivatives can be obtained in high yield.

The following examples further illustrate this invention without limiting the same.

EXAMPLE 1

222 g of 2-(1',1',3',3'-tetramethylbutyl)hydroquinone was dissolved in 1 liter of glacial acetic acid. To this, 177 g of 2-methyl-2,4-pentanediol was added, and then, a mixed solution of 500 ml of glacial acetic acid and 490 g of conc. (98%) sulfuric acid was dropwise added thereto over about 1 hour while ice-cooling. After the completion of the addition, the temperature was gradually raised to 30° C over about 30 minutes, and, then moderate stirring effected at 30° C for 5 hours to precipitate crystals. Water was added to complete the precipitation, and then the crystals were filtered out and recrystallized from n-hexane to obtain 320 g of crystals having a melting point of 125° to 126° C. The melting point and the infrared absorption spectrum of the crystals precisely agreed with those of 2,2,4-trimethyl-6-hydroxy-7-(1',1',3',3'-tetramethylbutyl)chroman which had been separately synthesized according to the process described in British patent specification No. 1,141,812.

EXAMPLE 2

The same procedures as in Example 1 were repeated except for using 197 g of 2-t-butyl-hydroquinone in place of the 2-(1',1',3',3'-tetramethylbutyl)hydroquinone used in Example 1 to obtain 220 g of 2,2,4-trimethyl-6-hydroxy-7-t-butylchroman.

While the invention has been described in detail and with reference to specific embodiments thereof, it will be apparent to one skilled in the art that various changes and modifications can be made therein without departing from the spirit and scope thereof.

What is claimed is:

1. A process for producing a 2,2,4-trimethyl-6-hydroxy-7-substituted chroman which comprises reacting a 2-substituted hydroquinone with 2-methyl-2,4-pentanediol in the presence of a Friedel-Crafts catalyst, said substituent being selected from the group consisting of
   i. a long straight chain alkyl group having 6 to 18 carbon atoms,
   ii. a branched chain alkyl group having 3 to 18 carbon atoms,
   iii. a straight chain alkenyl group having 6 to 18 carbon atoms,
   iv. a branched chain alkenyl group having 3 to 18 carbon atoms,
   v. a phenyl group,
   vi. a naphthyl group,
   vii. a phenyl group substituted with one or more members of the group consisting of an alkyl group having 1 to 12 carbon atoms, a nitro group, an amino group, an acyl group having 2 to 13 carbon atoms, a carboxyl group or a sulfo group, or
   viii. a naphthyl group substituted with one or more members of the group consisting of an alkyl group having 1 to 12 carbon atoms, a nitro group, an amino group, an acyl group having 2 to 13 carbon atoms, a carboxyl group or a sulfo group.

2. The process of claim 1, wherein said 2,2,4-trimethyl-6-hydroxy-7-substituted chroman is selected from the group consisting of 2,2,4,7-tetramethyl-6-hydroxychroman, 2,2,4-trimethyl-6-hydroxy-7-butenylchroman, 2,2,4-trimethyl-6-hydroxy-7-n-hexylchroman, 2,2,4-trimethyl-6-hydroxy-7-isopropylchroman, 2,2,4-trimethyl-6-hydroxy-7-t-butylchroman, 2,2,4-trimethyl-6-hydroxy-7-(1',1',3',3'-tetramethylbutyl)chroman, 2,2,4-trimethyl-6-hydroxy-7-phenylchroman, 2,2,4-trimethyl-6-hydroxy-7-nitrophenylchroman and 2,2,4-trimethyl-6-hydroxy-7-sulfonaphthylchroman.

3. The process of claim 1, wherein the 2-methyl-2,4-pentanediol is added in an amount of about 1 to about 3 mols per mol of the 2-substituted hydroquinone.

4. The process of claim 1, wherein said Friedel-Crafts catalyst is selected from the group consisting of aluminum chloride, ferric chloride, stannic chloride, zinc chloride, sulfuric acid and polyphosphoric acid.

5. The process of claim 1, wherein said reaction is conducted in a solvent capable of dissolving the starting materials.

6. The process of claim 1, wherein said reaction is conducted in a solvent selected from the group consisting of an alcohol, an ethylene glycol monoalkyl ether, an amide, an ether, an organic acid or mixtures thereof.

7. The process of claim 1, wherein said reaction is conducted in a solvent selected from the group consisting of methanol, ethanol, isopropanol, acetamide, dimethylformamide, diethyl ether, dioxane, formic acid, oxalic acid, acetic acid, a monomethyl, monoethyl or monobutyl ethylene glycol ether or mixtures thereof.

8. The process as claimed in claim 1, wherein said reaction is conducted at a molar ratio of about 0.5 to about 5.0 moles of said Friedel-Crafts catalyst per mole of 2-substituted hydroquinone.

* * * * *